United States Patent [19]

Wade

[11] Patent Number: 4,572,910
[45] Date of Patent: Feb. 25, 1986

[54] TRIAZOLO[1,5-C]PYRIMIDINES SUBSTITUTED BY NITROGEN-CONTAINING HETEROCYCLIC RINGS

[75] Inventor: James J. Wade, Oakdale, Minn.

[73] Assignee: Riker Laboratories, Inc., St. Paul, Minn.

[21] Appl. No.: 471,836

[22] Filed: Mar. 3, 1983

[51] Int. Cl.$^4$ ............... A61K 31/505; A61K 31/535; A61K 31/54; C07D 471/04
[52] U.S. Cl. .................................. 514/222; 514/227; 514/258; 544/227; 544/258; 544/58.2; 544/60; 544/61; 544/81; 544/82; 544/118; 544/122; 544/263; 544/295
[58] Field of Search ................. 544/58.2, 61, 81, 118, 544/263; 424/246, 248.4; 514/222, 227, 258

[56] References Cited

U.S. PATENT DOCUMENTS 4,269,980  5/1981  Hardy et al. ................... 544/256

FOREIGN PATENT DOCUMENTS 1205144  6/1957  France .
859287  1/1961  United Kingdom .
873223  1/1961  United Kingdom .
897870  5/1962  United Kingdom .
898409  6/1962  United Kingdom .

OTHER PUBLICATIONS

G. W. Miller et al.; J. Chem. Soc., 1963, 5642 and 3357.
W. Broadbent et al., J. Chem. Soc., 1963, 3369.
Temple et al., J. Org. Chem., 1963, 33, 530.
D. J. Brown et al., Aust. J. Chem., 1978, 31, 2505.
D. J. Brown et al., Aust. J. Chem., 1979, 32, 1585.
D. J. Brown et al., Aust. J. Chem., 1980, 33, 1147.

Primary Examiner—Richard L. Raymond
Attorney, Agent, or Firm—Donald M. Sell; James A. Smith; Robert W. Sprague

[57] ABSTRACT

1,2,4-Triazolo[1,5-c]pyrimidines substituted at the 5 or 7 positions through a nitrogen atom which is part of a heterocyclic ring have been found to have potent bronchodilator activity. Methods for inducing bronchodilation, pharmaceutical compositions and synthetic processes are also disclosed.

14 Claims, No Drawings

TRIAZOLO[1,5-C]PYRIMIDINES SUBSTITUTED BY NITROGEN-CONTAINING HETEROCYCLIC RINGS

TECHNICAL FIELD

The present invention relates to triazolo[1,5-c]pyrimidines, and more specifically to 1,2,4-triazolo[1,5-c]pyrimidines. The pharmacological use of the compounds of the invention as bronchodilators, pharmaceutical compositions comprising the compounds, and processes for the preparation of the compounds are also within the scope of the invention.

BACKGROUND OF THE INVENTION

Some 1,2,4-triazolo[1,5-c]pyrimidines are known to the art. Certain 1,2,4-triazolo[1,5-c]pyrimidines are disclosed as being bronchodilators in the patents discussed below, the compounds being referred to therein as triazolo[2,3-c]pyrimidines:

United Kingdom Patent No. 859,287 discloses 2-amino-1,2,4-triazolo[1,5-c]pyrimidines which are substituted on the pyrimidine ring at the 5, 7 and 8 positions by certain combinations of substituents selected from hydrogen, alkyl, halogen-substituted alkyl, hydroxy-substituted alkyl, alkoxy-substituted alkyl, alkenyl, cycloalkyl, amino, alkylamino, dialkylamino, phenyl, alkylthio, alkoxy and halogen substituents. United Kingdom Patent No. 898,407 discloses processes for preparing certain of these compounds by subjecting the corresponding 1,2,4-triazolo[4,3-c]pyrimidines to an acid treatment, to an alkaline treatment, or to a heat treatment.

United Kingdom Patent No. 873,223 discloses 2-amino or 2-acetamido-1,2,4-triazolo[1,5-c]pyrimidines which are substituted on the pyrimidine ring at the 5, 7 and 8 positions by certain combinations of substituents selected from hydrogen, alkyl, halogen-substituted alkyl, alkoxy-substituted alkyl, alkenyl, cycloalkyl, alkylthio and halogen substituents.

United Kingdom Patent No. 897,870 discloses 2-alkylamino-1,2,4-triazolo[1,5-c]pyrimidines, 2-dialkylamino-1,2,4-triazolo[1,5-c]pyrimidines, and 1,2,4-triazolo[1,5-c]pyrimidines containing a piperidino or morpholino substituent bonded at the 2-position through the nitrogen atom, which compounds are substituted on the pyrimidine ring at the 5, 7 and 8 positions by certain combinations of substituents selected from hydrogen, alkyl, halogen-substituted alkyl, hydroxy-substituted alkyl, alkenyl and halogen substituents.

The following related articles discloses the synthesis of certain 1,2,4-triazolo[1,5-c]pyrimidines as potential bronchodilators:

G. W. Miller et al., *J. Chem. Soc.,* 1963, 5642, discloses 2-amino- or 2-acetamido-1,2,4-triazolo[1,5-c]pyrimidines (referred to therein as triazolo[2,3-c]pyrimidines) which are substituted on the pyrimidine ring by, for example, hydrogen and alkyl substituents. Certain of these compounds are said to be bronchodilators.

G. W. Miller et al., *J. Chem. Soc.,* 1963, 3357, discloses 1,2,4-triazolo[1,5-c]pyrimidines (referred to therein as triazolo[2,3-c]pyrimidines) which are substituted at the 2-position by hydroxy, halogen, alkoxy, amino or substituted amino substituents and on the pyrimidine ring by alkyl substituents, or alkyl and halogen-substituted alkyl substituents.

W. Broadbent et al., *J. Chem. Soc.,* 1963, 3369, discloses 1,2,4-triazolo[1,5-c]pyrimidines (referred to therein as triazolo[2,3-c]pyrimidines) which are substituted at the 2-position by a mercapto, alkylthio, alkylsulphonyl, or dialkylamino substituent, and on the pyrimidine ring by alkyl substituents or alkyl and halogen-substituted alkyl substituents.

Still other 1,2,4-triazolo[1,5-c]pyrimidines are disclosed in the following articles and patents.

Temple et al., *J. Org. Chem.,* 1963, 33, 530, discloses the compound 8-amino-7-chloro-s-triazolo[1,5-c]pyrimidine-2(3H)-one.

D. J. Brown et al., *Aust. J. Chem.,* 1978, 31, 2505, discloses 1,2,4-triazolo[1,5-c]pyrimidines which are substituted at the 2-position by hydrogen or an alkyl substituent, and on the pyrimidine ring by hydrogen and/or alkyl substituents.

D. J. Brown et al., *Aust. J. Chem.,* 1979, 32, 1585, discloses 1,2,4-triazolo[1,5-c]pyrimidines which are substituted at the 2-position by hydrogen or an alkyl substituent, and on the pyrimidine ring at the 5-position by a halogen, hydrazino, alkyl or alkylthio substituent, and at the 7-position by an alkyl substituent.

D. J. Brown et al., *Aust. J. Chem.,* 1980, 33, 1147, discloses pyrimidines which are substituted at the 2-position by hydrogen or an alkyl or phenyl substituent, and on the pyrimidine ring at the 5-position by halogen, dimethylaminomethyleneamino, hydroxyaminomethyleneamino or 5-acetoxyaminomethyleneamino, and at the 7-position by hydrogen or an alkyl substituent.

U.S. Pat. No. 4,269,980 discloses 5-, 7- and 8-(optionally substituted phenyl)-1,2,4-triazolo[1,5-c]pyrimidines. These compounds may be substituted at the 2-position by hydrogen or an alkyl substituent and are anxiolytic agents.

DETAILED DESCRIPTION OF THE INVENTION

The present invention relates to 1,2,4-triazolo[1,5-c]pyrimidines which are bronchodilators. The invention also relates to a method for inducing bronchodilation in a mammal using a 1,2,4-triazolo[1,5,-c]pyrimidine of the invention, and to pharmaceutical compositions comprising an effective amount of a 1,2,4-triazolo[1,5-c]pyrimidine of the invention and a pharmaceutically acceptable carrier. The invention also relates to synthetic processes useful for preparing the 1,2,4-triazolo[1,5-c]pyrimidines of the invention.

Specifically, the present invention relates to compounds of the formula I

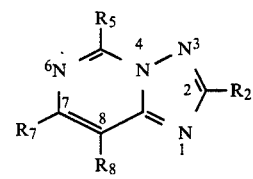

wherein $R_2$ is hydrogen or lower alkyl; at least one of $R_5$ and $R_7$ is

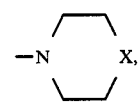

wherein each X is independently oxygen, sulfur, sulfinyl, sulfonyl, methylene (—CH₂—), imido (—NH—) or N-lower alkylimido

and one of $R_5$ and $R_7$ may also be hydrogen, lower alkyl or phenyl; and $R_8$ is hydrogen, lower alkyl or phenyl; and pharmaceutically acceptable salts thereof.

"Lower alkyl" as used in the instant specification and claims designates straight or branched-chain alkyl groups containing one to about four carbon atoms. Preferred lower alkyl substituents are methyl and ethyl.

The presently preferred compounds of the invention are those wherein X is sulfur or oxygen and $R_8$ is hydrogen. These compounds are preferred because of their generally higher potency in protecting against histamineinduced contraction of isolated guinea pig tracheal tissue. This assay is discussed in greater detail below.

Specific examples of preferred compounds which are active in the aforementioned assay at concentrations of 5 ug per ml or lower are:
2-methyl-5-(4-thiomorpholino)-1,2,4-triazolo[1,5-c]pyrimidine
2-ethyl-7-methyl-5-(4-thiomorpholino)-1,2,4-triazolo[1,5-c]pyrimidine
5,7-bis(4-morpholino)-1,2,4-triazolo[1,5-c]pyrimidine
5-(4-morpholino)-7-(4-thiomorpholino)-1,2,4-triazolo[1,5-c]pyrimidine
2-ethyl-5-methyl-7-(4-thiomorpholino)-1,2,4-triazolo[1,5-c]pyrimidine
2-ethyl-5-methyl-7-(4-morpholino)-1,2,4-triazolo[1,5-c]pyrimidine
2,5-diethyl-7-(4-thiomorpholino)-1,2,4-triazolo[1,5-c]pyrimidine
2-ethyl-7-(4-morpholino)-5-n-propyl-1,2,4-triazolo[1,5-c]pyrimidine
7-(4-morpholino)-5-n-propyl-1,2,4-triazolo[1,5-c]pyrimidine
2-ethyl-5-n-propyl-7-(4-thiomorpholino)-1,2,4-triazolo[1,5-c]pyrimidine
5-n-propyl-7-(4-thiomorpholino)-1,2,4-triazolo[1,5-c]pyrimidine
5-ethyl-7-(4-morpholino)-1,2,4-triazlo[1,5-c]pyrimidine
5-ethyl-2-methyl-7-(4-morpholino)-1,2,4-triazolo[1,5-c]pyrimidine
2,5-diethyl-7-(4-morpholino)-1,2,4-triazolo[1,5-c]pyrimidine The bronchodilator activity of the compounds of Formula I was assessed by the measurement of effects on isolated tracheal spirals. This is a well-known and long established in vitro test method. The bronchodilator activity was determined according to the following procedure: Female guinea pigs were sacrificed and each trachea removed and cut into a spiral strip. This strip was mounted in a constant temperature (37° C.) muscle bath having a volume of approximately 15 ml. The bathing medium was Krebs-Henseleit solution. Movement of the tracheal strip was measured by means of an isometric transducer connected to an electric recorder. The bath was aerated with a mixture of 95% carbon dioxide and 5% oxygen. Contractions were induced in the strips by the addition of a suitable amount of histamine, acetylcholine or barium chloride. The amount of a given compound of Formula I (measured in ug/ml) required to provide greater than 75% relaxation of drug-induced contraction is considered an effective concentration. For comparison, a well known standard bronchodilator, aminophylline, requires concentrations of 50 ug/ml versus histamine, 100 ug/ml versus acetylcholine and 10 ug/ml versus barium chloride to provide greater than 75% relaxation.

The compounds of Formula I which were most active in the in vitro test, including most of those listed above as preferred compounds, were tested in vivo in the guinea pig for oral activity in the so-called histamine aerosol method described in U.S. Pat. No. 3,248,292. This test was modified slightly in that a 0.1% aqueous solution of histamine was used as the agent for inducing bronchial constriction. Oral doses were measured in mg/kg of body weight of the guinea pig.

Some of the compounds of Formula I were also found to have activity as mucolytics in an in vitro test for mucus production in which rats are orally dosed with compound prior to sacrifice. The trachea is then isolated and incubated with radiolabelled glucosamine and the effect of compounds on the incorporation of glucosamine into extracellular mucus is determined. An active compound reduces incorporation of glucosamine. Specific examples of preferred compounds which are active in this assay are:
7-Methyl-5-(4-morpholino)-1,2,4-triazolo[1,5-c]pyrimidine
2,7-Dimethyl-5-(4-methyl-1-piperazinyl)-1,2,4-triazolo[1,5-c]pyrimidine
2,7-Dimethyl-5-(1-piperazinyl)-1,2,4-triazolo[1,5-c]pyrimidine.

The compounds of Formula I may be administered to mammals in order to obtain bronchodilation. The compounds may be administered orally, parenterally or by inhalation. Preferably they are administered orally in tablets or capsules. The usual effective human dose will be in the range of 0.1 to 50 mg/kg of body weight.

Salts of compounds of Formula I are generally prepared by reaction with an equimolar amount of a relatively strong acid, preferably an inorganic acid such as hydrochloric, sulfuric or phosphoric acid, in a polar solvent. Isolation of the salt is facilitated by the addition of a solvent in which the salt is insoluble, an example of such a solvent is diethyl ether.

The compounds of Formula I, either as the free base or in the form of a pharmaceutically acceptable acidaddition salt, can be combined with conventional pharmaceutical diluents and carriers to form such dosage forms as tablets, capsules, suspensions, solutions, suppositories and the like.

The pharmaceutical carrier employed may be, for example, either a solid or liquid. Examples of solid carriers are lactose, terra alba, sucrose, talc, gelatin, agar, pectin, acacia, magnesium stearate, stearic acid, and the like. Liquid carriers include syrup, peanut oil, olive oil, water and the like. Similarly, the carrier or diluent can include a time delay material well known to the art, such as glyceryl monostearate or glyceryl distearate, these being employed alone or, for example, in combination with a wax.

The compounds of Formula I may be prepared by several synthetic routes. One such route is that shown in Scheme I below. This route is useful in preparing compounds wherein $R_5$ is hydrogen, lower alkyl or phenyl; $R_7$ is

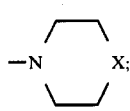

and $R_2$, $R_8$ and X are as defined previously. Each "alk" appearing in Scheme I is independently lower alkyl.

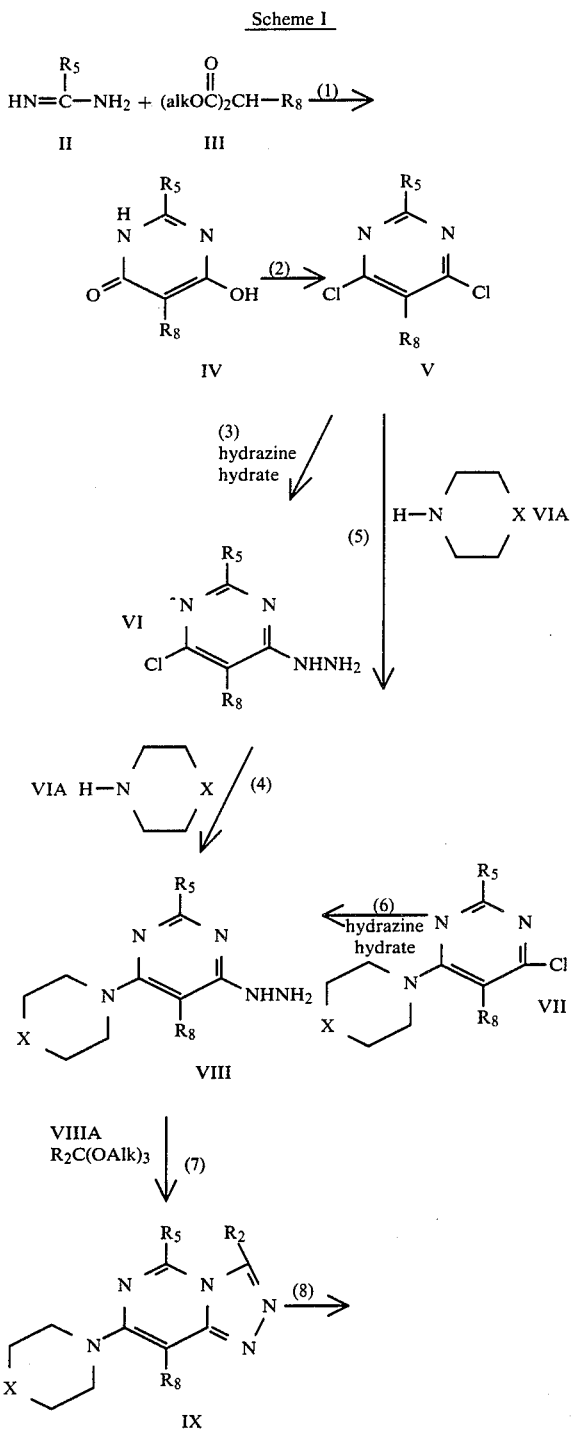

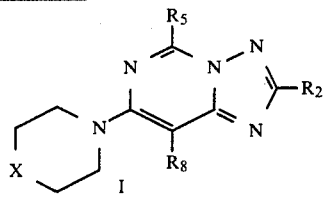

The reactions of steps (1), (2) and (3) have previously been reported for the preparation of compounds wherein $R_5$ is hydrogen, methyl or ethyl and $R_8$ is hydrogen or methyl. Thus, most of the compounds of formulas IV, V, and VI are known. Heterocyclic compounds of formulas VII, VIII and IX are novel. The known methods were used to carry out the reactions of steps (1), (2) and (3). Specifically, steps (1) and (2) were carried out as described in H. R. Henze et al., J. Org. Chem., 1952, 17, 1320 and H. R. Henze et al., J. Org. Chem., 1953, 18, 653, and step (3) was carried out as described in J. Chesterfield et al., J. Chem. Soc., 1955, 3478. Example 1 hereinbelow details these steps.

Step (4) is carried out by reacting the optionally substituted 4-chloro-6-hydrazinopyrimidine of Formula VI with a heterocyclic amine of the formula VIA. The reactants are heated together without solvent or optionally (and preferably) in any solvent which does not participate in the reaction such as water. Two equivalents of the heterocyclic amine are preferably used. Alternatively, one equivalent of the heterocyclic amine may be replaced by an inorganic base to neutralize the hydrogen chloride, but lower yields are obtained. The reaction mixture is heated at a temperature up to or at its reflux temperature. A temperature is chosen which provides an adequate reaction rate. When water is used as the solvent, the temperature is generally in the range of 80° to 110° C. Good yields of the desired products are isolated by conventional methods such as filtration, extraction or chromatography. The novel intermediate of Formula VIII, which may also be prepared alternatively by following steps (5) and (6), are solids whose structural assignments are confirmed by infrared and nuclear magnetic resonance spectral analyses.

Step (5) is carried out by reacting optionally substituted 4,6-dichloropyrimidines of Formula V with heterocyclic amines of the formula VIA. This reaction is carried out by heating the reactants without solvent, or preferably in any solvent which does not participate in the reaction. Two equivalents of the heterocyclic amine are preferably used, one to react with the chloropyrimidine and the other to neutralize the hydrogen chloride by-product. Alternatively, an inorganic base may be used to neutralize the hydrogen chloride by-product, but lower yields of the desired product are generally obtained. Heating is at a temperature up to and including the reflux temperature of the mixture. A temperature is chosen which provides an adequate reaction rate. If water is used as a solvent, the mixture is generally heated at its reflux temperature. Good yields of the desired product are isolated by conventional methods such as filtration, extraction or chromatography. The novel intermediates of Formula VII are solids. Structural assignments are confirmed by infrared and nuclear magnetic resonance spectral analyses.

Step (6) is carried out by reacting the novel substituted 4-chloro-6-heterocyclicaminopyrimidine of Formula VII with hydrazine hydrate. The reaction is facile and is generally carried out at moderate temperatures, for example, from −20° C. to the reflux temperature of the solvent. The reaction is generally carried out by adding two equivalents of hydrazine hydrate to a solution of the pyrimidine. The solvent will generally be a lower alkanol. The product is separated by conventional methods such as filtration, extraction or chromatography and is the same novel intermediate of Formula VIII obtained from step (4).

Step (7) is carried out by reacting the intermediate of Formula VIII with an orthoester of formula VIIA. Such orthoesters are well known and readily available. Examples of suitable orthoesters include trimethyl orthoformate, triethyl orthoformate, triethyl orthoacetate, triethyl orthopropionate and the like. Since the orthoesters are liquids, it is convenient to mix the intermediates of Formula VIII with an excess of orthoester and to heat the mixture at reflux until reaction is complete. Good yields of the desired solid intermediates of Formula IX which are novel substituted 1,2,4-triazolo[4,3-c]pyrimidines are obtained by conventional methods.

In step (8), the 1,2,4-triazolo[4,3-c]pyrimidines of Formula IX are heated with an aqueous acid and thereby converted to the desired compounds of the invention of Formula I wherein $R_5$ is

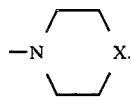

The preferred aqueous acids are carboxylic acids such as formic acid, acetic acid and propionic acid. The reaction mixture is generally heated at reflux for up to several days. The desired product is isolated by conventional methods. The structural assignments are made based on infrared and nuclear magnetic resonance spectral analyses. The products are generally white crytalline solids.

In some cases step (8) may be accomplished by continued heating of the reactants of step (7). This conversion occurs most readily when $R_5$ is hydrogen, and is carried out by using dimethyl sulfoxide as the solvent for the combined steps (7) and (8) as described in Example 104.

Synthetic Scheme II shows a method for the preparation of compounds of Formula I wherein both $R_5$ and $R_7$ are

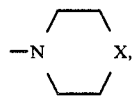

wherein X is as defined previously and may be the same or different in the two heterocyclic amino groups; and $R_2$ and $R_8$ are as defined previously. Alk is as defined previously.

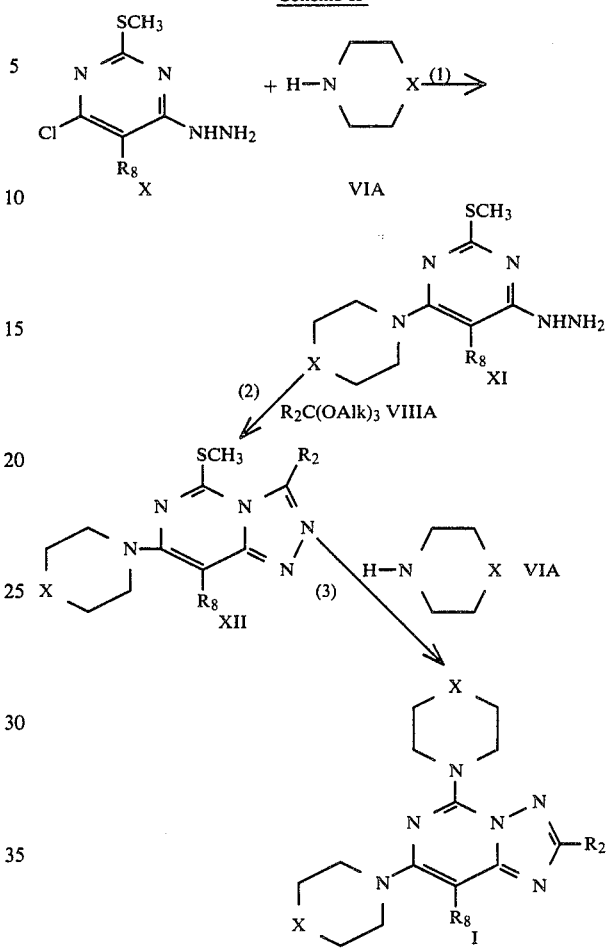

Step (1) of Scheme II requires reaction of the 4-chloro-6-hydrazino-2-methylthiopyrimidine of Formula X with a heterocyclic amine of the Formula VIA. Generally the 4-chloro-6-hydrazino-2-methylthiopyrimidines of Formula X are known compounds or may be prepared by conventional methods. The reaction is generally conducted in an inert solvent, preferably water, optionally in the presence of an acid acceptor such as a tertiary organic amine, for example, triethylamine. The reaction is best carried out using two equivalents of the amine of Formula VIA, one to react with the 4-chloro-6-hydrazino-2-methylthiopyrimidine and one to react with the hydrochloric acid which results. The mixture is heated at reflux for several hours, then cooled. Usually the novel intermediate of Formula XI is obtained directly as a solid precipitate. Alternatively, it is obtained by extraction or chromatographic techniques.

Step (2) of Scheme II is carried out by mixing the intermediate of Formula XI with an orthoester of Formula VIIIA. The reaction is carried out as described for step (7) of Scheme I. The product obtained is a novel intermediate of Formula XII. The product of this step generally is a mixture which is separated by chromatography, preferably high pressure liquid chromatography, to provide the crystalline solid. Occasionally the desired isomer is obtained in such high purity that chromatographic separation is unnecessary.

Step (3) of Scheme II requires heating of the intermediate of Formula XII in an excess of the heterocyclic amine of the Formula VIA, optionally in an inert solvent such as diglyme or dioxane. The reaction is generally carried out at the reflux temperature of the mixture. The product is isolated by conventional methods such as filtration, extraction or chromatography.

An alternative scheme, used for preparing compounds of Formula I wherein R₅ is

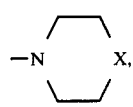

wherein X is as defined previously; R₇ is hydrogen or lower alkyl; and R₂ and R₈ are as defined previously, is shown in Scheme III.

Scheme III

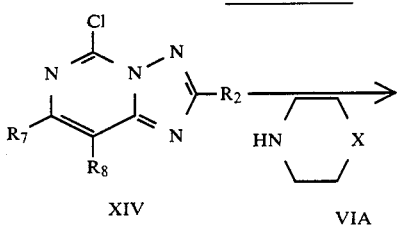

XIV      VIA

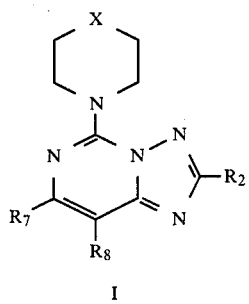

I

The compounds of Formula XIV are generally known or may be prepared by conventional methods. Known methods may be employed to vary substituents R₂ and R₇. The reaction of Scheme III occurs readily at moderate temperatures, for example from 0° C. up to the reflux temperature of the solvent. It is carried out either by adding the heterocyclic amine of Formula VIA to a solution of the intermediate of Formula XIV or vice versa. The solvent may be inert solvent, for example water or dioxane. The product of Formula I prepared in Scheme III is obtained in good yields by conventional isolation methods.

Synthetic Scheme IV illustrated below is a method for preparation of compounds of Formula I wherein R₂ and R₇ are independently hydrogen or lower alkyl; R₅ is

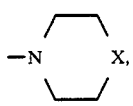

wherein X is as defined previously; and R₈ is as defined previously.

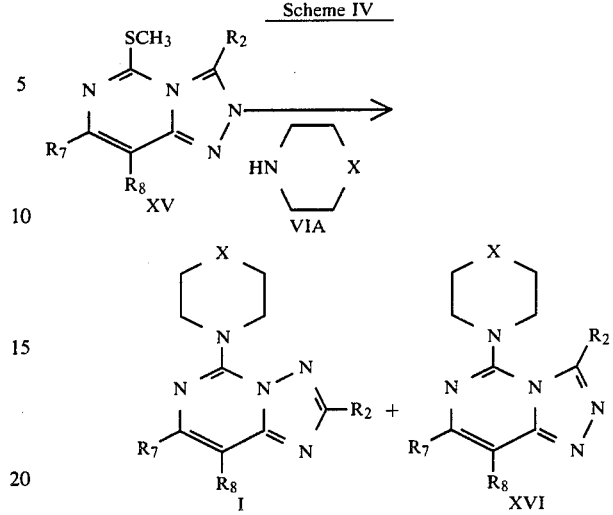

The reaction of Scheme IV is similar to reaction of step (3) of Scheme II. The intermediates of Formula XV are known or may be prepared from known starting materials using known methods. The products of Scheme IV are prepared and isolated as described for that step.

The following examples are provided to illustrate the methods used in the invention. They are not intended to limit the invention.

EXAMPLE 1

Preparation of 2,7-Diethyl-5-(4-methyl-1-piperazinyl)-1,2,4-triazolo[1,5-c]pyrimidine according to Scheme I, Steps (1), (2), (3), (4), (7) and (8)

Part A1

Preparation of Propionamidine

Hydrogen chloride gas was bubbled into a mixture of 110 g (2.00 mole) of propionitrile and 70.0 g (2.19 mole) of methanol while cooling with an ice bath and maintaining the reaction mixture under a nitrogen stream until 78.5 g (2.15 mole) of hydrogen chloride had been added. The reaction flask was stoppered and stirred at 20° C. for 4.5 days. To this mixture was added 150 ml of methanol. Ammonia gas was bubbled into the mixture (accompanied by cooling) for two hours until the mixture was basic to litmus paper. The flask was stoppered and stirred for about 16 hours. The solids were removed by filtration, washed with methanol and the washings and filtrate were concentrated by evaporation. The residue was dissolved in 400 ml of ethanol. The solution was cooled and then filtered and the filtrate was concentrated by evaporation. The residue was again dissolved in ethanol, cooled, filtered and the filtrate was evaporated to provide a residue which crystallized to provide 114 g (53%) of propionamidine hydrochloride.

Part A2

Alternative Preparation of Propionamidine

A mixture of 35 g (0.2 mole) of triethyl orthopropionate and 15.4 g (0.2 mole) of ammonium acetate was reacted as described by Taylor, et. al., J. Am. Chem. Soc., 1960, 82, 3138, by heating the mixture at reflux for 45 minutes. The product was isolated by distilling off ethanol, followed by filtration to provide 17 g of propionamidine acetate, m.p. 165°–167° C. An additional 3 g was obtained by concentrating the filtrate and adding acetone to provide a 77% yield overall. The structure was confirmed by nuclear magnetic resonance and infrared spectral analyses.

Part B1

Preparation of 4,6-Dihydroxy-2-ethylpyrimidine according to Step (1)

To a cooled (using an ice-bath), stirred solution of 25% sodium methoxide (1200 ml, 5.55 mole) was added a slurry of 200 g (1.85 mole) of propionamidine hydrochloride in 300 ml methanol. Next, 244 g (1.85 mole) of dimethyl malonate was added and the mixture was permitted to warm to about 20° C., after which it was stirred for 16 hours. The mixture was evaporated in vacuo and water (about 2 l) was then added. This mixture was neutralized with concentrated hydrochloric acid to provide a white precipitate which was separated by filtration to provide 230 g (96%) of 4,6-dihydroxy-2-ethylpyrimidine, m.p. 312°–315° C. The structural assignment was confirmed by infrared and nuclear magnetic resonance spectral analyses.

Part B2

Alternative Preparation of 4,6-Dihydroxy-2-ethylpyrimidine

Using the procedure of Example 1, Part B1, 18.5 g (0.14 mole) of propionamidine acetate and 90 ml of 25% sodium methoxide were reacted with dimethyl malonate (0.14 mole) to provide 16.5 g (89.5%) of 4,6-dihydroxy-2-ethylpyrimidine according to Step (1).

Part C

Preparation of 4,6-Dichloro-2-ethylpyrimidine

A mixture of 150 g (1.15 mole) of 4,6-dihydroxy-2-ethylpyrimidine and 1073 g (7.0 mole, 640 ml) of phosphorus oxychloride was heated at reflux for 6 hours, cooled and evaporated in vacuo to provide a brown oil as the residue. The residue was poured into 1500 ml of an ice-water mixture. The mixture was extracted thrice with 400 ml portions of diethyl ether. The combined ether extracts were washed sequentially with water (200 ml), 5% sodium hydroxide solution (twice with 200 ml portions) and saturated sodium chloride solution (200 ml) and were then dried over magnesium sulfate. Evaporation of the ether provided an oil which was distilled to provide 41 g (70%) of 4,6-dichloro-2-ethylpyrimidine, b.p. 55–60 C/1.5 to 4 mm Hg. The structural assignment was confirmed by infrared and nuclear magnetic resonance spectral analyses.

Part D

Preparation of 4-Chloro-2-ethyl-6-hydrazinylpyrimidine according to Step (3)

To a stirred, cold (0° C.) solution of 60 g (0.34 mole) of 4,6-dichloro-2-ethylpyrimidine in 500 ml of methanol was added 35 g (0.7 mole) of hydrazine hydrate while maintaining the temperature below 10° C. Stirring was continued for 2 hours after completion of the addition, the temperature being maintained at 0° C. The mixture was allowed to warm to about 20° C. and was stirred for 16 hours. The white solid was collected by filtration and the filtrate was partially evaporated to provide a second crop. The combined solids were washed with water and air dried to provide 51 g (77%) of 4-chloro-2-ethyl-6-hydrazinylpyrimidine, m.p. 147°–150° C.

Part E

Preparation of 2-Ethyl-6-hydrazinyl-4-(4-methyl-1-piperazinyl)pyrimidine according to Step (4)

A mixture of 8.3 g (0.05 mole) of 4-chloro-2-ethyl-6-hydrazinylpyrimidine and 11 g (0.10 mole) of 1-methylpiperazine in 250 ml of water was heated at reflux for 16 hours and was then cooled and extracted with chloroform. The extracts were dried over magnesium sulfate and were then evaporated to provide 8.3 g (70%) of 2-ethyl-6-hydrazinyl-4-(4-methyl-1-piperazinyl)pyrimidine.

Part F

Preparation of 3,5-Diethyl-7-(4-methyl-1-piperazinyl)-1,2,4-triazolo[4,3-c]pyrimidine according to Step (7)

A mixture of 8.3 g (0.045 mole) of 2-ethyl-6-hydrazinyl-4-(4-methyl-1-piperazinyl)pyrimidine and 75 ml of triethyl orthopropionate was heated at reflux for 48 hours. After cooling the mixture was evaporated in vacuo. Diethyl ether was added to the residue and the mixture was cooled. The precipitate was collected by filtration to provide 4.5 g (37%) of 3,5-diethyl-7-(4-methyl-1-piperazinyl)-1,2,4-triazolo[4,3-c]pyrimidine. Recrystallization from ethyl acetate-hexane and then from ethyl acetate-cyclohexane provided a white crystalline product, m.p. 128°–131° C. Analysis for $C_{14}H_{22}N_6$: Calculated: %C, 61.3; %H, 8.1; %N, 30.6; Found: %C, 59.8; %H, 8.2; %N, 30.1. The structural assignment was confirmed by nuclear magnetic resonance and infrared spectral analyses.

Part G

Preparation of 2,5-Diethyl-7-(4-methyl-1-piperazinyl)-1,2,4-triazolo[1,5-c]pyrimidine according to step (8)

A mixture of 3.3 g of 3,5-diethyl-7-(4-methyl-1-piperazinyl)-1,2,4-triazolo[4,3-c]pyrimidine and 50 ml of 97% formic acid was heated at reflux for 18 hours. The mixture was cooled and evaporated in vacuo to provide a residue which was diluted with 100 ml of water and carefully neutralized with sodium bicarbonate. The solution was extracted with chloroform. The extracts were dried and then concentrated to provide an oil which solidified and was collected by filtration, washed with water and dried. Recrystallization from hexane provided off-white crystalline solid 2,5-diethyl-7-(4-methyl-1-piperazinyl)-1,2,4-triazolo[1,5-c]pyrimidine, m.p. 87°–88° C. Analysis: Calculated for $C_{14}H_{22}N_6$: %C, 61.3; %H, 8.1; %N, 30.6; Found: %C, 60.6; %H, 8.1, %N, 30.6. The structural assignment was confirmed by infrared and nuclear magnetic resonance spectral analyses.

EXAMPLES 2–21

Using the method of Part E, Example 1, the indicated intermediate amines of Formula VIA were reacted with the indicated known 4-chloro-2-alkyl-6-hydrazinyl-pyrimidines of Formula VI to provide the novel intermediates of Formula VIII (Table I).

TABLE I

| Example | Amine Intermediate | Pyrimidine Intermediate of Formula VI | Intermediate of Formula VIII | Melting Point (in °C.) |
|---|---|---|---|---|
| 2 | piperidine (HN⟨ ⟩) | 6-chloro-2-ethyl-4-hydrazino pyrimidine (CH$_2$CH$_3$; Cl; NHNH$_2$) | 2-ethyl-6-piperidino-4-hydrazino pyrimidine | none taken (yield 66%) |
| 3 | thiomorpholine (HN⟨ ⟩S) | " | 2-ethyl-6-thiomorpholino-4-hydrazino pyrimidine | 158–160 (yield 94.5%) |
| 4 | morpholine (HN⟨ ⟩O) | " | 2-ethyl-6-morpholino-4-hydrazino pyrimidine | 129–133 (yield 75%) |
| 5 | morpholine (HN⟨ ⟩O) | 6-chloro-2-propyl-4-hydrazino pyrimidine ((CH$_2$)$_2$CH$_3$) | 2-propyl-6-morpholino-4-hydrazino pyrimidine | 112–115 |
| 6 | 4-methylpiperazine (CH$_3$N⟨ ⟩NH) | 6-chloro-2-propyl-4-hydrazino pyrimidine | 2-propyl-6-(4-methylpiperazino)-4-hydrazino pyrimidine | none taken (yield 84%) |
| 7 | thiomorpholine (HN⟨ ⟩S) | 6-chloro-2-propyl-4-hydrazino pyrimidine | 2-propyl-6-thiomorpholino-4-hydrazino pyrimidine | 144–146 (yield 71%) |
| 8 | piperidine (HN⟨ ⟩) | 6-chloro-2-methyl-5-methyl-4-hydrazino pyrimidine (CH$_3$; Cl; CH$_3$; NHNH$_2$) | 2-propyl-6-piperidino-4-hydrazino pyrimidine ((CH$_2$)$_2$CH$_3$) | none taken (yield 85%) |
| 9 | morpholine (HN⟨ ⟩O) | 6-chloro-2-methyl-4-hydrazino pyrimidine (CH$_3$) | 2-methyl-6-morpholino-4-hydrazino pyrimidine (CH$_3$) | none taken (yield 68%) |

TABLE I-continued

| Example | Amine Intermediate | Pyrimidine Intermediate of Formula VI | Intermediate of Formula VIII | Melting Point (in °C.) |
|---|---|---|---|---|
| 10 | thiomorpholine | 6-chloro-2,5-dimethyl-4-hydrazino pyrimidine with CH3 | 6-thiomorpholino-2,5-dimethyl-4-hydrazino pyrimidine | 183–185 |
| 11 | morpholine | 6-chloro-2,5-dimethyl-4-hydrazino pyrimidine | 6-morpholino-2,5-dimethyl-4-hydrazino pyrimidine | none taken (yield 66%) |
| 12 | thiomorpholine | 6-chloro-2-methyl-4-hydrazino pyrimidine | 6-thiomorpholino-2-methyl-4-hydrazino pyrimidine | 203–204 |
| 13 | N-methylpiperazine | 6-chloro-2-methyl-4-hydrazino pyrimidine | 6-(4-methylpiperazino)-2-methyl-4-hydrazino pyrimidine | 174–177 |
| 14 | morpholine | 6-chloro-4-hydrazino pyrimidine | 6-morpholino-4-hydrazino pyrimidine | 155–157 |
| 15 | thiomorpholine | 6-chloro-4-hydrazino pyrimidine | 6-thiomorpholino-4-hydrazino pyrimidine | 147–149 |
| 16 | morpholine | 6-chloro-2-isopropyl-4-hydrazino pyrimidine | 6-morpholino-2-isopropyl-4-hydrazino pyrimidine | 122–123 |
| 17 | thiomorpholine | 6-chloro-2-isopropyl-4-hydrazino pyrimidine | 6-thiomorpholino-2-isopropyl-4-hydrazino pyrimidine | 124–126 |

TABLE I-continued

| Example | Amine Intermediate | Pyrimidine Intermediate of Formula VI | Intermediate of Formula VIII | Melting Point (in °C.) |
|---|---|---|---|---|
| 18 | morpholine (HN-O ring) | 2-(CH$_2$)$_3$CH$_3$, 4-Cl, 6-NHNH$_2$ pyrimidine | 2-(CH$_2$)$_3$CH$_3$, 4-morpholinyl, 6-NHNH$_2$ pyrimidine | none taken |
| 19 | thiomorpholine (HN-S ring) | 2-(CH$_2$)$_3$CH$_3$, 4-Cl, 6-NHNH$_2$ pyrimidine | 2-(CH$_2$)$_3$CH$_3$, 4-thiomorpholinyl, 6-NHNH$_2$ pyrimidine | none taken |
| 20 | morpholine (HN-O ring) | 2-CH$_2$CH(CH$_3$)$_2$, 4-Cl, 6-NHNH$_2$ pyrimidine | 2-CH$_2$CH(CH$_3$)$_2$, 4-morpholinyl, 6-NHNH$_2$ pyrimidine | (oil) |
| 21 | thiomorpholine (HN-S ring) | 2-CH$_2$CH(CH$_3$)$_2$, 4-Cl, 6-NHNH$_2$ pyrimidine | 2-CH$_2$CH(CH$_3$)$_2$, 4-thiomorpholinyl, 6-NHNH$_2$ pyrimidine | (oil) |

EXAMPLES 22–59

Using the method of Part F, Example 1, the indicated intermediates of Formula VIII were reacted with the indicated trialkyl orthoesters to provide the novel compounds of Formula IX (Table II).

TABLE II

| | Intermediate of Formula VIII | | | | Intermediate of Formula IX | | | | Calculated: % C; % H; % N Found: % C; % H; % N |
|---|---|---|---|---|---|---|---|---|---|
| Ex. | R$_5$ | R$_8$ | X | Ortho Ester | R$_2$ | R$_5$ | R$_8$ | X | (m.p. in °C.) |
| 22 | CH$_3$ | H | SO$_2$ | triethyl orthoformate | H | CH$_3$ | H | SO$_2$ | 44.9; 4.9; 26.2<br>44.9; 4.9; 26.3<br>(299–300) |
| 23 | CH$_3$ | H | SO$_2$ | triethyl orthoacetate | CH$_3$ | CH$_3$ | H | SO$_2$ | 47.0; 5.4; 25.0<br>47.1; 5.4; 24.9<br>(307–308) |
| 24 | CH$_2$CH$_2$CH$_3$ | H | O | triethyl orthoformate | H | CH$_2$CH$_2$CH$_3$ | H | O | 58.3; 6.9; 28.3<br>58.2; 7.0; 28.4<br>(200–202) |
| 25 | CH$_2$CH$_2$CH$_3$ | H | O | triethyl orthopropionate | CH$_2$CH$_3$ | CH$_2$CH$_2$CH$_3$ | H | O | 61.1; 7.7; 25.4<br>60.9; 7.9; 25.7<br>(179–181) |
| 26 | CH$_2$CH$_2$CH$_3$ | H | S | triethyl orthoformate | H | CH$_2$CH$_2$CH$_3$ | H | S | 54.7; 6.5; 26.6<br>54.6; 6.5; 26.9<br>(208–209) |
| 27 | CH$_2$CH$_2$CH$_3$ | H | S | triethyl orthopropionate | CH$_2$CH$_3$ | CH$_2$CH$_2$CH$_3$ | H | S | 57.7; 7.3; 24.0<br>57.7; 7.5; 24.4<br>(143–144) |
| 28 | CH$_2$CH$_2$CH$_3$ | H | CH$_2$ | triethyl orthopropionate | CH$_2$CH$_3$ | CH$_2$CH$_2$CH$_3$ | H | CH$_2$ | (as H$_2$SO$_4$ salt):<br>48.5; 6.8; 18.9<br>48.4; 7.0; 19.0<br>(190–192) |
| 29 | CH$_3$ | H | S | triethyl orthoformate | H | CH$_3$ | H | S | 51.0; 5.6; 29.8<br>51.0; 5.5; 29.6<br>(234–237) |
| 30 | CH$_2$CH$_3$ | H | CH$_2$ | triethyl orthopropionate | CH$_2$CH$_3$ | CH$_2$CH$_3$ | H | CH$_2$ | 64.8; 8.2; 27.0<br>65.1; 8.3; 27.2 |

TABLE II-continued

| | Intermediate of Formula VIII | | | | Intermediate of Formula IX | | | | Calculated: % C; % H; % N<br>Found: % C; % H; % N |
|---|---|---|---|---|---|---|---|---|---|
| Ex. | $R_5$ | $R_8$ | X | Ortho Ester | $R_2$ | $R_5$ | $R_8$ | X | (m.p. in °C.) |
| 31 | $CH_2CH_3$ | H | S | triethyl orthopropionate | $CH_2CH_3$ | $CH_2CH_3$ | H | S | (120–122)<br>56.3; 6.9; 25.2<br>56.1; 7.2; 25.5 |
| 32 | $CH_2CH_3$ | H | S | triethyl orthoacetate | $CH_3$ | $CH_2CH_3$ | H | S | (149–150)<br>54.7; 6.5; 26.6<br>54.4; 6.7; 26.7 |
| 33 | $CH_2CH_3$ | H | S | triethyl orthoformate | H | $CH_2CH_3$ | H | S | (168–170)<br>53.0; 6.0; 28.1<br>52.6; 6.2; 28.2 |
| 34 | $CH_2CH_3$ | H | O | triethyl orthoacetate | $CH_3$ | $CH_2CH_3$ | H | O | (243–245)<br>58.3; 6.9; 28.3<br>58.2; 7.0; 28.5 |
| 35 | $CH_2CH_3$ | H | O | triethyl orthopropionate | $CH_2CH_3$ | $CH_2CH_3$ | H | O | (200–203)<br>59.7; 7.3; 26.8<br>59.6; 7.4; 27.0 |
| 36 | $CH_2CH_3$ | H | O | triethyl orthoformate | H | $CH_2CH_3$ | H | O | (173–174)<br>56.6; 6.5; 30.0<br>56.6; 6.4; 30.3 |
| 37 | $CH_3$ | H | O | trimethyl orthoformate | H | $CH_3$ | H | O | (223–224)<br>54.8; 6.0; 31.9<br>54.7; 6.0; 31.4 |
| 38 | $CH_3$ | H | O | triethyl orthoacetate | $CH_3$ | $CH_3$ | H | O | (208–210)<br>56.6; 6.5; 30.0<br>56.7; 6.3; 30.3 |
| 39 | $CH_3$ | H | O | triethyl orthopropionate | $CH_2CH_3$ | $CH_3$ | H | O | (171–173)<br>58.3; 6.9; 28.3<br>57.9; 7.0; 28.3 |
| 40 | $CH_3$ | H | S | triethyl orthoacetate | $CH_3$ | $CH_3$ | H | S | (169–172)<br>53.0; 6.0; 28.1<br>53.1; 6.3; 28.3 |
| 41 | $CH_3$ | H | S | triethyl orthopropionate | $CH_2CH_3$ | $CH_3$ | H | S | (223–225)<br>54.8; 6.5; 26.6<br>54.4; 6.7; 26.8 |
| 42 | $CH_3$ | $CH_3$ | S | triethyl orthoformate | H | $CH_3$ | $CH_3$ | S | (161–163)<br>53.0; 6.0; 28.1<br>53.2; 6.3; 28.4 |
| 43 | $CH_3$ | $CH_3$ | S | triethyl orthoacetate | $CH_3$ | $CH_3$ | $CH_3$ | S | (182–184)<br>54.7; 6.5; 26.6<br>54.4; 6.6; 26.9 |
| 44 | $CH_3$ | $CH_3$ | S | triethyl orthopropionate | $CH_2CH_3$ | $CH_3$ | $CH_3$ | S | (184–185)<br>56.3; 6.9; 25.2<br>56.4; 7.1; 25.1 |
| 45 | $CH_3$ | $CH_3$ | $SO_2$ | triethyl orthoformate | H | $CH_3$ | $CH_3$ | $SO_2$ | (129–130)<br>46.9; 5.4; 24.9<br>47.0; 5.3; 25.2 |
| 46 | $CH_2CH_3$ | H | S | trimethyl orthobutyrate | $CH_2CH_2CH_3$ | $CH_2CH_3$ | H | S | (234–236)<br>57.7; 7.3; 24.0<br>57.6; 7.5; 24.2 |
| 47 | $CH_2CH_3$ | H | O | trimethyl orthobutyrate | $CH_2CH_2CH_3$ | $CH_2CH_3$ | H | O | (163–165)<br>61.1; 7.7; 25.4<br>61.0; 7.9; 25.8 |
| 48 | $CH_2CH_3$ | H | O | trimethyl orthoisobutyrate | $CH(CH_3)_2$ | $CH_2CH_3$ | H | O | (164–166)<br>61.1; 7.7; 25.4<br>61.0; 7.7; 25.3 |
| 49 | $CH_2CH_3$ | H | S | trimethyl orthoisobutyrate | $CH(CH_3)_2$ | $CH_2CH_3$ | H | S | (136–137)<br>57.7; 7.3; 24.0<br>57.8; 7.3; 24.2 |
| 50 | $CH_2CH_2CH_3$ | H | S | trimethyl orthobutyrate | $CH_2CH_2CH_3$ | $CH_2CH_2CH_3$ | H | S | (143–144)<br>59.0; 7.6; 22.9<br>59.0; 7.5; 23.1 |
| 51 | $CH_2CH_2CH_3$ | H | O | trimethyl orthobutyrate | $CH_2CH_2CH_3$ | $CH_2CH_2CH_3$ | H | O | (134–135)<br>62.3; 8.0; 24.2<br>62.2; 8.1; 24.1 |
| 52 | $CH_2CH_2CH_3$ | H | S | trimethyl orthoisobutyrate | $CH(CH_3)_2$ | $CH_2CH_2CH_3$ | H | S | (139–140)<br>59.0; 7.6; 22.9<br>59.1; 7.7; 23.0 |
| 53 | $CH_2CH_2CH_3$ | H | O | trimethyl orthoisobutyrate | $CH(CH_3)_2$ | $CH_2CH_2CH_3$ | H | O | (134–136)<br>62.3; 8.0; 24.2<br>62.4; 8.1; 24.6 |
| 54 | $CH(CH_3)_2$ | H | O | triethyl orthoformate | H | $CH(CH_3)_2$ | H | O | (116–117)<br>(as $H_2SO_4$ Salt):<br>41.7; 5.5; 20.3<br>41.6; 5.7; 20.6 |
| 55 | $CH(CH_3)_2$ | H | O | triethyl orthopropionate | $CH_2CH_3$ | $CH(CH_3)_2$ | H | O | (177–178)<br>(as $H_2SO_4$ Salt):<br>45.0; 6.2; 18.8<br>44.9; 6.3; 19.0 |
| 56 | $CH(CH_3)_2$ | H | O | trimethyl | $CH_2CH_2CH_3$ | $CH(CH_3)_2$ | H | O | (167–168)<br>(as $H_2SO_4$ Salt): |

TABLE II-continued

| | Intermediate of Formula VIII | | | | Intermediate of Formula IX | | | | Calculated: % C; % H; % N Found: % C; % H; % N |
|---|---|---|---|---|---|---|---|---|---|
| Ex. | $R_5$ | $R_8$ | X | Ortho Ester | $R_2$ | $R_5$ | $R_8$ | X | (m.p. in °C.) |
| | | | | orthobutyrate | | | | | 46.5; 6.5; 18.1 46.2; 6.5; 18.3 (162-163) |
| 57 | $CH(CH_3)_2$ | H | S | triethyl orthoacetate | $CH_3$ | $CH(CH_3)_2$ | H | S | (as $H_2SO_4$ Salt): 41.6; 5.6; 18.7 41.6; 5.8; 18.8 (170-172) |
| 58 | $CH(CH_3)_2$ | H | S | triethyl orthopropionate | $CH_2CH_3$ | $CH(CH_3)_2$ | H | S | (as $H_2SO_4$ Salt): 43.2; 6.0; 18.0 43.1; 6.1; 18.2 (174-175) |
| 59 | $CH(CH_3)_2$ | H | O | triethyl orthoformate | H | $CH(CH_3)_2$ | H | O | (as $H_2SO_4$ Salt): 41.7; 5.5; 20.3 41.6; 5.7; 20.6 (177-178) |

EXAMPLES 60-96

Using the method of Part G, Example 1, the indicated intermediates of Formula IX were heated with formic acid to provide the indicated compounds of Formula I (Table III).

TABLE III

| Ex. No. | Product of Formula IX; Product of Formula I | | | | Product of Formula I Calculated: % C; % H; % N Found: % C; % H; % N |
|---|---|---|---|---|---|
| | $R_2$ | $R_5$ | $R_8$ | X | |
| 60 | $CH_2CH_3$ | $CH_2CH_3$ | H | $CH_2$ | 64.8; 8.2; 27.0 65.1; 8.3; 27.0 m.p. 90-92° C. |
| 61 | $CH_2CH_3$ | $CH_2CH_3$ | H | S | 56.3; 6.9; 25.2 56.1; 7.1; 25.0 m.p. 119-120° C. |
| 62 | $CH_3$ | $CH_2CH_3$ | H | S | 54.7; 6.5; 26.6 54.8; 6.8; 26.5 m.p. 164-165° C. |
| 63 | H | $CH_2CH_3$ | H | S | 53.0; 6.0; 28.1 52.9; 6.3; 28.4 m.p. 228-230° C. |
| 64 | $CH_3$ | $CH_2CH_3$ | H | O | 58.3; 6.9; 28.3 58.3; 7.0; 28.3 m.p. 159-160° C. |
| 65 | $CH_2CH_3$ | $CH_2CH_3$ | H | O | 59.7; 7.3; 26.8 59.7; 7.3; 26.9 m.p. 118-119° C. |
| 66 | H | $CH_2CH_3$ | H | O | 56.6; 6.5; 30.0 56.8; 6.5; 30.1 m.p. 168-170° C. |
| 67 | H | $CH_3$ | H | $O_2S$ | 44.9; 4.9; 26.2 44.9; 4.9; 26.2 m.p. 251-253° C. |
| 68 | $CH_3$ | $CH_3$ | H | $O_2S$ | 47.0; 5.4; 25.0 46.8; 5.4; 24.4 m.p. 229-233° C. |
| 69 | H | $(CH_2)_2CH_3$ | H | O | 58.3; 6.9; 28.3 58.5; 7.0; 28.6 m.p. 153-155° C. |
| 70 | $CH_2CH_3$ | $(CH_2)_2CH_3$ | H | O | 61.1; 7.7; 25.4 61.2; 7.7; 25.6 m.p. 130-131° C. |
| 71 | H | $(CH_2)_2CH_3$ | H | S | 54.7; 6.5; 26.6 54.9; 6.5; 26.9 m.p. 145-150° C. |
| 72 | $CH_2CH_3$ | $(CH_2)_2CH_3$ | H | S | 57.7; 7.3; 24.0 57.6; 7.3; 24.2 m.p. 101-103° C. |
| 73 | $CH_2CH_3$ | $(CH_2)_2CH_3$ | H | $CH_2$ | 65.9; 8.5; 25.6 65.8; 8.6; 25.8 m.p. 60-62° C. |
| 74 | H | $CH_3$ | H | S | 51.0; 5.5; 29.8 51.0; 5.7; 30.2 m.p. 154-156° C. |
| 75 | H | $CH_3$ | H | O | 54.8; 6.0; 31.9 54.7; 5.8; 32.4 |
| 76 | $CH_3$ | $CH_3$ | H | O | m.p. 159-161.5° C. 56.5; 6.5; 30.0 56.7; 6.6; 30.6 |
| 77 | $CH_2CH_3$ | $CH_3$ | H | O | m.p. 182-183° C. 58.3; 6.9; 28.3 58.3; 7.0; 28.7 |
| 78 | $CH_3$ | $CH_3$ | H | S | m.p. 146-147° C. 53.0; 6.0; 28.1 52.7; 6.1; 28.0 |
| 79 | $CH_2CH_3$ | $CH_3$ | H | S | m.p. 170-172° C. 54.7; 6.5; 26.7 54.6; 6.7; 27.1 |
| 80 | H | $CH_3$ | $CH_3S$ | | m.p. 124-125° C. 53.0; 6.0; 28.1 52.9; 6.2; 28.4 |
| 81 | $CH_3$ | $CH_3$ | $CH_3S$ | | m.p. 150-152° C. 54.7; 6.5; 26.2 54.8; 6.5; 26.6 |
| 82 | $CH_2CH_3$ | $CH_3$ | $CH_3S$ | | m.p. 128-130° C. 56.3; 6.9; 25.2 56.3; 6.9; 25.4 |
| 83 | H | $CH_3$ | $CH_3O_2S$ | | m.p. 80-81° C. 46.9; 5.4; 24.9 46.9; 5.3; 25.1 |
| 84 | $CH(CH_3)_2$ | $CH_2CH_3$ | H | S | m.p. 219-224° C. (as $H_2SO_4$ Salt): 43.7; 6.0; 18.0 43.1; 6.0; 18.4 |
| 85 | $CH(CH_3)_2$ | $CH_2CH_3$ | H | O | m.p 193-194° C. (as $H_2SO_4$ Salt): 45.0; 6.2; 18.8 44.9; 6.3; 19.1 |
| 86 | $(CH_2)_2CH_3$ | $CH_2CH_3$ | H | O | m.p. 189-190° C. (as $H_2SO_4$ Salt): 45.0; 6.2; 18.8 44.9; 6.3; 19.1 |
| 87 | $(CH_2)_2CH_3$ | $CH_2CH_3$ | H | S | m.p. 170-172° C. (as $H_2SO_4$ Salt): 43.2; 6.0; 18.0 43.0; 6.1; 18.3 |
| 88 | $(CH_2)_2CH_3$ | $CH_3(CH_2)_2$ | H | S | m.p. 152-153° C. (as $H_2SO_4$ Salt): 44.6; 6.2; 17.4 44.7; 6.4; 17.5 |
| 89 | $(CH_2)_2CH_3$ | $(CH_2)_2CH_3$ | H | O | m.p. 143-145° C. (as $H_2SO_4$ Salt): 46.5; 6.5; 18.1 46.6; 6.7; 18.4 |
| 90 | $CH(CH_3)_2$ | $(CH_2)_2CH_3$ | H | S | m.p. 169-171° C. (as $H_2SO_4$ Salt): 44.6; 6.2; 17.4 44.8; 6.4; 17.6 |
| 91 | $CH(CH_3)_2$ | $CH_3(CH_2)_2$ | H | O | m.p. 172-173° C. (as $H_2SO_4$ Salt): 46.5; 6.5; 18.1 |

TABLE III-continued

| Ex. No. | Product of Formula IX; Product of Formula I | | | Product of Formula I Calculated: % C; % H; % N Found: % C; % H; % N |
|---|---|---|---|---|
| | R$_2$ | R$_5$ | R$_8$ X | |
| 92 | CH$_2$CH$_3$ | CH(CH$_3$)$_2$ | H O | 46.4; 6.7; 18.3<br>m.p. 156–157° C.<br>61.1; 7.7; 25.4 |
| 93 | (CH$_2$)$_2$CH$_3$ | CH(CH$_3$)$_2$ | H O | 61.0; 7.9; 25.9<br>m.p. 128–129° C.<br>62.3; 8.0; 24.2 |
| 94 | CH$_3$ | CH(CH$_3$)$_2$ | H S | 61.3; 8.1; 24.0<br>m.p. 85–86° C.<br>56.3; 6.9; 25.3<br>56.1; 6.9; 25.8<br>m.p. 170–172° C. |
| 95 | CH$_2$CH$_3$ | (CH$_3$)$_2$CH | H S | 57.7; 7.3; 24.0<br>57.3; 7.1; 24.3<br>m.p. 142–143° C. |
| 96 | H | CH(CH$_3$)$_2$ | H O | (as H$_2$SO$_4$ Salt):<br>41.7; 5.5; 20.3<br>41.0; 5.2; 20.3<br>m.p. 179–182° C. |

EXAMPLE 97

Preparation of 2-n-Propyl-7-(4-thiomorpholino)-1,2,4-triazolo[1,5-c]pyrimidine

A mixture of 8.00 g (37.9 mmole) of 4-hydrazino-6-(4-thiomorpholino)pyrimidine and 20 ml of trimethyl ortho-n-butyrate was heated at its reflux temperature for about 60 hours, cooled, and the solid was isolated by filtration. The product was washed with diethyl ether, then recrystallized twice from a benzene-hexane mixture accompanied by treatment with decolorizing charcoal to provide off-white 2-n-propyl-7-(4-thiomorpholino)-1,2,4-triazolo[1,5-c]pyrimidine, m.p. 137°–138° C. Most (4.6 g, 17.5 mmole) of this product was dissolved in 100 ml of ethanol and 1.75 g (17.1 mmole) of sulfuric acid was added. The solution was diluted to 300 ml with diethyl ether and allowed to stand for two hours. The precipitate was collected by filtration, washed with diethyl ether and dried to provide the dihydrogen sulfate salt, m.p. 134°–137° C. Analysis: Calculated for C$_{12}$H$_{17}$N$_5$S.H$_2$SO$_4$: %C, 39.9; %H, 5.3; %N, 19.4; Found: %C, 39.5; %H, 5.2; %N, 19.5. The structural assignment was confirmed by infrared spectral analysis.

EXAMPLES 98–103

Using the method of Example 97, the indicated intermediates of Formula VIII were reacted with the indicated orthoesters to provide the indicated compounds of Formula I (Table IV).

TABLE IV

| Example Number | Intermediate of Formula VIII | | | Orthoester | Product of Formula I | | | | Calculated: % C; % H; % N<br>Found: % C; % H; % N<br>(m.p. in C) |
|---|---|---|---|---|---|---|---|---|---|
| | R$_5$ | R$_8$ | X | | R$_2$ | R$_5$ | R$_8$ | X | |
| 98 | H | H | O | trimethyl orthoisobutyrate | CH(CH$_3$)$_2$ | H | H | O | 58.3; 6.9; 28.3<br>58.1; 6.9; 28.5<br>(154–155) |
| 99 | H | H | S | triethyl orthoacetate | CH$_3$ | H | H | S | 51.0; 5.6; 29.8<br>50.9; 5.5; 30.1<br>(145–148) |
| 100 | H | H | S | triethyl orthopropionate | CH$_2$CH$_3$ | H | H | S | 53.0; 6.1; 28.1<br>52.7; 6.0; 28.3<br>(125–126) |
| 101 | H | H | S | trimethyl orthobutyrate | CH$_2$CH$_2$CH$_3$ | H | H | S | 54.7; 6.5; 26.6<br>54.6; 6.4; 26.7<br>(137–138) |
| 102 | H | H | O | triethyl orthoformate | H | H | H | O | 52.7; 5.4; 34.1<br>52.2; 5.3; 34.2<br>(202–204) |
| 103 | H | H | O | triethyl orthopropionate | CH$_2$CH$_3$ | H | H | O | 56.6; 6.5; 30.0<br>56.5; 6.3; 30.2<br>(164–165) |

EXAMPLE 104

Preparation of 2,5-Di(isopropyl)-7-(4-thiomorpholino)-1,2,4-triazolo[1,5-c]pyrimidine A mixture of 4.00 g (15.8 mmole) of 4-hydrazino-2-isopropyl-6-(4-thiomorpholino)pyrimidine, 2.40 g (16.2 mmole) of trimethyl isobutyrate, 0.95 g (15.8 mmole) of acetic acid and 40 ml of dimethyl sulfoxide was heated at 120° C. for about 65 hours and then poured into 200 ml of ice water. The mixture was basified with 10 percent aqueous sodium hydroxide and extracted four times with 50 ml of chloroform. The extracts were washed six times with 150 ml of water, dried over magnesium sulfate and evaporated to provide a dark oil. Nuclear magnetic resonance spectral analysis indicated that the oil was chiefly the desired product. The product was chromatographed on 70 g of silica gel, eluting sequentially with 600 ml of dichloromethane, one liter of 50:50 ethyl acetate:dichloromethane, and ethyl acetate, 100 ml fractions being taken. Fractions 7, 8 and 9 provided 3.35 g (70%) of brown oil. The oil was dissolved in 50 ml of ethanol, and sulfuric acid (1.09 g, 10.7 mmole) and 200 ml of diethyl ether were then added sequentially. The precipitate was collected by filtration, washed with diethyl ether and dried. The product was off-white solid 2,5-di(isopropyl)-7-(4-thiomorpholino)-1,2,4-triazolo-[1,5-c]pyrimidine dihydrogen sulfate, m.p. 192°–194° C. Analysis: Calculated for C$_{15}$H$_{23}$N$_5$S.H$_2$SO$_4$: %C, 44.6; %H, 6.3; %N, 17.4; Found: %C, 44.6; %H, 6.3; %N, 17.5. The structure was confirmed by infrared and nuclear magnetic resonance spectral analyses.

EXAMPLES 105–127

Using the method of Example 104, the indicated intermediates of Formula VIII were reacted with the indicated orthoesters to provide the indicated compounds of Formula I (Table V).

TABLE V

| Example Number | Intermediate of Formula VIII | | | | Product of Formula I | | | | Calculated: % C; % H; % N Found: % C; % H; % N (m.p. in C.) |
|---|---|---|---|---|---|---|---|---|---|
| | $R_5$ | $R_8$ | X | Orthoester | $R_2$ | $R_5$ | $R_8$ | X | |
| 105 | $CH_2CH_3$ | H | S | trimethyl orthoisovalerate | $CH_2CH(CH_3)_2$ | $CH_2CH_3$ | H | S | (as $H_2SO_4$ Salt): 44.6; 6.2; 17.4 44.5; 6.5; 17.6 (155–156) |
| 106 | $CH(CH_3)_2$ | H | S | trimethyl orthoisovalerate | $CH_2CH(CH_3)_2$ | $CH(CH_3)_2$ | H | S | (as $H_2SO_4$ Salt): 46.0; 6.5; 16.8 45.9; 6.7; 16.9 (169–170) |
| 107 | $CH_2CH_3$ | H | S | trimethyl orthovalerate | $(CH_2)_3CH_3$ | $CH_2CH_3$ | H | S | (as $H_2SO_4$ Salt): 44.6; 6.2; 17.4 44.3; 6.2; 17.7 (132–135) |
| 108 | $(CH_2)_2CH_3$ | H | S | trimethyl orthovalerate | $(CH_2)_3CH_3$ | $(CH_2)_2CH_3$ | H | S | (as $H_2SO_4$ Salt): 46.0; 6.5; 16.8 46.0; 6.4; 17.1 (152–153) |
| 109 | $CH_2CH(CH_3)_2$ | H | S | trimethyl orthoisobutyrate | $CH(CH_3)_2$ | $CH_2CH(CH_3)_2$ | H | S | 60.1; 7.9; 21.9 59.7; 7.9; 21.7 (94–97) |
| 110 | $CH_2CH(CH_3)_2$ | H | O | triethyl orthopropionate | $CH_2CH_3$ | $CH_2CH(CH_3)_2$ | H | O | 62.2; 8.0; 24.2 62.0; 7.7; 24.2 (119–122) |
| 111 | $CH_2CH(CH_3)_2$ | H | O | trimethyl orthoisobutyrate | $CH(CH_3)_2$ | $CH_2CH(CH_3)_2$ | H | O | 63.3; 8.3; 23.1 63.2; 8.0; 23.1 (93–95) |
| 112 | $CH_2CH(CH_3)_2$ | H | O | trimethyl orthovalerate | $(CH_2)_3CH_3$ | $CH_2CH(CH_3)_2$ | H | O | 64.3; 8.6; 22.1 63.7; 8.2; 21.9 (85–88) |
| 113 | $(CH_2)_3CH_3$ | H | S | triethyl orthoacetate | $CH_3$ | $(CH_2)_3CH_3$ | H | S | 57.7; 7.7; 24.0 57.3; 7.3; 24.1 (123–126) |
| 114 | $(CH_2)_3CH_3$ | H | S | trimethyl orthobutyrate | $(CH_2)_2CH_3$ | $(CH_2)_3CH_3$ | H | S | 60.3; 7.9; 22.0 59.9; 8.0; 21.9 (66–68) |
| 115 | $(CH_2)_3CH_3$ | H | S | trimethyl orthoisovalerate | $CH_2CH(CH_3)_2$ | $(CH_2)_3CH_3$ | H | S | 61.4; 8.2; 21.1 60.9; 8.3; 21.1 (50–53) |
| 116 | $CH_2CH(CH_3)_2$ | H | O | triethyl orthoformate | H | $CH_2CH(CH_3)_2$ | H | O | 59.7; 7.3; 26.8 59.6; 7.2; 26.9 (123–126) |
| 117 | $(CH_2)_3CH_3$ | H | S | triethyl orthopropionate | $CH_2CH_3$ | $(CH_2)_3CH_3$ | H | S | 59.0; 7.6; 22.9 59.2; 7.7; 23.3 (110–112) |
| 118 | $CH_2CH_3$ | H | O | trimethyl orthovalerate | $(CH_2)_3CH_3$ | $CH_2CH_3$ | H | O | 62.3; 8.0; 24.2 62.1; 8.0; 24.3 (87–89) |
| 119 | $(CH_2)_2CH_3$ | H | O | trimethyl orthovalerate | $(CH_2)_3CH_3$ | $(CH_2)_2CH_3$ | H | O | 63.3; 8.3; 23.1 63.1; 8.2; 23.3 (105–106) |
| 120 | $(CH_2)_3CH_3$ | H | O | triethyl orthoacetate | $CH_3$ | $(CH_2)_3CH_3$ | H | O | 61.1; 7.7; 25.4 61.0; 7.8; 25.3 (132–133) |
| 121 | $(CH_2)_3CH_3$ | H | O | triethyl orthopropionate | $CH_2CH_3$ | $(CH_2)_3CH_3$ | H | O | 62.3; 8.0; 24.2 62.1; 8.1; 24.2 (105–106) |
| 122 | $(CH_2)_3CH_3$ | H | O | trimethyl orthobutyrate | $(CH_2)_2CH_3$ | $(CH_2)_3CH_3$ | H | O | 63.3; 8.3; 23.1 63.3; 8.4; 23.2 (98–99) |
| 123 | $(CH_2)_3CH_3$ | H | O | trimethyl orthoisovalerate | $CH_2CH(CH_3)_2$ | $(CH_2)_3CH_3$ | H | O | 64.3; 8.6; 22.1 64.2; 8.4; 22.0 (73–75) |
| 124 | $CH_2CH(CH_3)_2$ | H | S | triethyl orthopropionate | $CH_2CH_3$ | $CH_2CH(CH_3)_2$ | H | S | 59.0; 7.6; 22.9 59.0; 7.2; 23.1 (124–126) |
| 125 | $(CH_2)_2CH_3$ | H | O | triethyl orthoisovalerate | $CH_2CH(CH_3)_2$ | $(CH_2)_2CH_3$ | H | O | 63.3; 8.3; 23.1 63.1; 7.9; 23.2 (53–55) |
| 126 | $CH_2CH(CH_3)_2$ | H | S | triethyl orthoformate | H | $CH_2CH(CH_3)_2$ | H | S | 56.3; 6.9; 25.2 56.3; 6.9; 25.4 (134–136) |
| 127 | $CH_2CH_3$ | H | O | trimethyl orthoisovalerate | $CH_2CH(CH_3)_2$ | $CH_2CH_3$ | H | O | 62.3; 8.0; 24.2 62.3; 7.9; 24.3 (50–52) |

EXAMPLE 128

Part A

Preparation of 4-Chloro-2-methyl-6-(4-morpholino)pyrimidine by Scheme I, Step (5)

A solution of 5.00 g (31.7 mmole) of 4,6-dichloro-2-methylpyrimidine and 6.00 g (68.9 mmole) of morpholine in 50 ml of water was heated on a steam cone for about 18 hours. The mixture was diluted with water and cooled. The resulting white solid was separated by filtration, washed with water and dried to provide 4.84 g (72%) of 4-chloro-2-methyl-6-(4-morpholino)pyrimidine. The structural assignment was confirmed by infrared and nuclear magnetic resonance spectral analyses.

Part B

Prepartion of 4-Hydrazino-2-methyl-6-(4-morpholino)pyrimidine by Scheme I, Step (6)

To a mixture of 4.70 g (22 mmole) of 4-chloro-2-methyl-6-(4-morpholino)pyrimidine in 50 ml of ethanol was added 2.2 g (44 mmole) of hydrazine hydrate and the mixture was heated at its reflux temperature for 16 hours. Cooling provided a precipitate which was separated by filtration and washed with ethanol to provide 3.15 g (68%) of white solid 4-hydrazino-2-methyl-6-(4-morpholino)pyrimidine. The structural assignment of the product was confirmed by infrared and nuclear magnetic resonance spectral analyses and comparison with the same compound made in Example 9.

EXAMPLES 129–131

Using the method of Example 128, Part A, the indicated intermediate of Formula V was reacted with the indicated amine of Formula VIA to provide the indicated intermediate of Formula VII. The intermediate of Formula VII was then reacted with hydrazine hydrate in accordance with the method of Example 128, Part B, to provide the indicated intermediate of Formula VIII (Table VI).

TABLE VI

| Example Number | Intermediate of Formula V | Heterocyclic Amine | Intermediate of Formula VII | Intermediate of Formula VIII |
|---|---|---|---|---|
| 129 | (structure) | morpholine | (structure) m.p. 147.5–150° C., White Solid | (structure) White Solid |
| 130 | (structure) | thiomorpholine-S,S-dioxide | (structure) m.p. 210–220° C., White Solid | (structure) m.p. 232–234° C., White Solid |
| 131 | (structure) | thiomorpholine-S,S-dioxide | (structure) m.p. about 200° C. | (structure) m.p. 250–253° C., White Solid |

EXAMPLE 132

Preparation According to Scheme II of 5,7-Bis(4-morpholino)-1,2,4-triazolo[1,5-c]pyrimidine

Part A

Preparation of 4-Hydrazinyl-2-methylthio-6-(4-morpholino)pyrimidine according to Scheme II, Step (1)

To a solution of 3.0 g (15.7 mmole) of 4-chloro-6-hydrazinyl-2-methylthiopyrimidine in 50 ml of water was added 2.8 g (32.2 mmole) of morpholine, and the mixture was heated at reflux for two days. Cooling gave a precipitate which was separated by filtration, washed with water and dried to provide off-white solid 4-hydrazinyl-2-methylthio-6-(4-morpholino)pyrimidine, m.p. 134°–144° C. The structural assignment was confirmed by infrared and nuclear magnetic resonance spectral analyses.

Part B

Preparation of 5-Methylthio-7-(4-morpholino)-1,2,4-triazolo[4,3-c]pyrimidine according to Scheme II, Step (2)

A mixture of 24.75 g (103 mmole) of 4-hydrazinyl-2-methylthio-6-(4-morpholino)pyrimidine and 200 ml of triethyl orthoformate was heated at 120° C. in an open flask for 60 hours. The mixture was cooled, then diluted with 300 ml of diethyl ether. The precipitate was separated by filtration, washed with ether and dried to provide 5-methylthio-7-(4-morpholino)-1,2,4-triazolo[4,3-c]pyrimidine, m.p. 212°–213° C. after two recrystallizations from chloroform-hexane.

Part C

Preparation of 5,7-Bis(4-morpholino)-1,2,4-triazolo[1,5-c]pyrimidine according to Scheme II, Step (3)

A mixture of 7.10 g (28.3 mmole) of 5-methylthio-7-(4-morpholino)-1,2,4-triazolo[1,5-c]pyrimidine and 35 ml of morpholine was heated at reflux for 16 hours. Cooling of the mixture provided a solid. The mixture was diluted to a total volume of 100 ml with diethyl ether, cooled and the product separated by filtration. Recrystallization with treatment with decolorizing charcoal from a mixture of benzene and hexane (1:1) provided white solid 5,7-bis(4-morpholino)-1,2,4-triazolo[1,5-c]pyrimidine, m.p. 176°–177° C. Analysis: Calculated for $C_{13}H_{18}N_6O_2$: %C, 53.8; %H, 6.2; %N, 29.0; Found: %C, 53.8; %H, 6.1; %N, 28.9. The structural assignment was confirmed by infrared and nuclear magnetic resonance spectral analyses.

EXAMPLES 133–135

Using the method of Example 132, Part A, the indicated intermediates of Formula XI were prepared from 4-chloro-6-hydrazino-2-methylthiopyrimidine and the indicated amine of Formula VIA (Table VII). The structures of the intermediates of Formula XI were confirmed by infrared and nuclear magnetic resonance spectral analyses.

TABLE VII

| Example | Amine Reactant of Formula VIA | Intermediate of Formula XI |
|---|---|---|
| 133 | HN(CH2CH2)2NCH3 | 2-SCH3, 4-NHNH2, 6-[N(CH2CH2)2NCH3] pyrimidine |
| 134 | HN(CH2CH2)2NH | 2-SCH3, 4-NHNH2, 6-[N(CH2CH2)2NH] pyrimidine |
| 135 | HN(CH2CH2)2S | 2-SCH3, 4-NHNH2, 6-[N(CH2CH2)2S] pyrimidine |

EXAMPLES 136–138

Using the method of Example 132, Part B, the indicated intermediates of Formula XII were prepared from the indicated intermediate of Formula XI (Table VIII). The structures of the intermediates of Formula XII were confirmed by infrared and nuclear magnetic resonance spectral analyses.

TABLE VIII

| Example | Intermediate of Formula XI | Intermediate of Formula XII |
|---|---|---|
| 136 | Example 133 | (triazolopyrimidine with SCH3 and N-methylpiperazinyl) |
| 137 | Example 134 | (triazolopyrimidine with SCH3 and piperazinyl) |
| 138 | Example 135 | (triazolopyrimidine with SCH3 and thiomorpholinyl) |

EXAMPLES 139–141

Using the method of Example 132, Part C, the indicated compounds of Formula I were prepared from the indicated intermediates of Formula XII and the indicated amine of Formula VIA (Table IX). Chromatographic separations were used to obtain the desired [1,5-c]isomers.

TABLE IX

| Example | Intermediate of Formula XII | Amine of Formula VIA | Product of Formula I | Calculated: % C; % H; % N<br>Found: % C; % H; % N |
|---|---|---|---|---|
| 139 | Example 136 | morpholine (HN with O) | morpholine-substituted triazolopyrimidine with CH₃N-piperazinyl group | 55.4; 7.0; 32.3<br>55.9; 6.9; 31.8<br>(m.p. 142–143.5° C.) |
| 140 | Example 137 | piperazine (HN—NH) | piperazine-substituted triazolopyrimidine with thiomorpholine group | 51.1; 6.3; 32.1<br>51.5; 6.3; 31.8<br>(m.p. 127–130° C.) |
| 141 | Example 138 | morpholine (HN with O) | morpholine-substituted triazolopyrimidine with thiomorpholine group | 51.0; 5.9; 27.4<br>50.7; 5.9; 27.6<br>(m.p. 169–170° C.) |

EXAMPLE 142

The Preparation of 2,7-Dimethyl-5-(1-piperazino)-1,2,4-triazolo[1,5-c]pyrimidine according to Scheme III A solution of the known compound 5-chloro-2,7-dimethyl-1,2,4-triazolo[1,5-c]pyrimidine (2.0 g, 11 mmole) in 50 ml of dioxane was added dropwise to a suspension of 120 g (140 mmole) of piperazine in 75 ml of dioxane. After stirring for 3 hours at 20° C., the mixture was diluted with 150 ml of water and then extracted with three 150 ml portions of chloroform. The extracts were washed with two 150 ml portions of water and two 100 ml portions of saturated sodium chloride solution and were then dried over magnesium sulfate. The extracts were evaporated to provide a residue which was recrystallized with treatment with decolorizing charcoal from a benzene-hexane mixture (1:3) to provide white solid 2,7-dimethyl-5-(1-piperazino)-1,2,4-triazolo[1,5-c]pyrimidine, m.p. 108°–110° C. Analysis: Calculated for $C_{11}H_{16}N_6$: %C, 56.9; %H, 6.9; %N, 36.2; Found: %C, 57.0; %H, 6.9; %N, 35.6.

EXAMPLES 143–156

Using the method of Example 142, the indicated compounds of Formula I were prepared from the indicated intermediates of Formula XIV and the indicated amines of Formula VIA (Table X).

TABLE X

| | Intermediate of Formula XIV | | | Amine of | Product of Formula I | | | | Calculated: % C; % H; % N |
|---|---|---|---|---|---|---|---|---|---|
| Example | $R_2$ | $R_7$ | $R_8$ | Formula VIA | $R_2$ | $R_5$ | $R_7$ | $R_8$ | Found: % C; % H; % N<br>(m.p. in C.) |
| 143 | CH₃ | CH₃ | H | HN\_/NCH₃ | CH₃ | —N\_/NCH₃ | CH₃ | H | 58.5; 7.4; 34.1<br>58.8; 7.3; 34.8<br>(106.5–107.5) |
| 144 | CH₃ | CH₃ | H | HN\_/SO₂ | CH₃ | —N\_/SO₂ | CH₃ | H | 47.0; 5.4; 24.9<br>47.0; 5.3; 25.4<br>(201–203) |

TABLE X-continued

| | Intermediate of Formula XIV | | | Amine of Formula VIA | Product of Formula I | | | | Calculated: % C; % H; % N Found: % C; % H; % N |
|---|---|---|---|---|---|---|---|---|---|
| Example | $R_2$ | $R_7$ | $R_8$ | | $R_2$ | $R_5$ | $R_7$ | $R_8$ | (m.p. in C.) |
| 145 | $CH_3$ | $CH_3$ | H | HN⟨⟩SO | $CH_3$ | −N⟨⟩SO | $CH_3$ | H | 49.8; 5.7; 26.4<br>50.0; 5.6; 26.8<br>(186–188) |
| 146 | $CH_3$ | $CH_3$ | H | HN⟨⟩S | $CH_3$ | −N⟨⟩S | $CH_3$ | H | 53.0; 6.1; 28.1<br>53.0; 6.1; 28.7<br>(133–134) |
| 147 | $CH_3$ | $CH_3$ | | HN⟨⟩O | $CH_3$ | −N⟨⟩O | $CH_3$ | H | 56.6; 6,5; 30.0<br>56.6; 6.4; 30.5<br>(142–144) |
| 148 | H | $CH_3$ | | HN⟨⟩S | H | −N⟨⟩S | $CH_3$ | H | 51.0; 5.6; 29.8<br>50.7; 5.6; 29.8<br>(99.5–100) |
| 149 | H | $CH_3$ | | HN⟨⟩SO | H | −N⟨⟩SO | $CH_3$ | H | 48.7; 5.2; 27.9<br>48.1; 5.2; 28.3<br>(188–190) |
| 150 | H | $CH_3$ | | HN⟨⟩$SO_2$ | H | −N⟨⟩$SO_2$ | $CH_3$ | H | 44.9; 4.9; 26.2<br>44.7; 5.0; 26.3<br>(222–223) |
| 151 | $CH_2CH_3$ | $CH_3$ | | HN⟨⟩S | $CH_2CH_3$ | −N⟨⟩S | $CH_3$ | H | 54.7; 6.5; 26.7<br>54.7; 6.7; 27.2<br>(106–107) |
| 152 | $CH_2CH_3$ | $CH_3$ | | HN⟨⟩SO | $CH_2CH_3$ | −N⟨⟩SO | $CH_3$ | H | 51.6; 6.1; 25.1<br>5.15; 6.3; 25.0<br>(146–148) |
| 153 | $CH_2CH_3$ | $CH_3$ | | HN⟨⟩$SO_2$ | $CH_2CH_3$ | −N⟨⟩$SO_2$ | $CH_3$ | H | 48.8; 5.8; 23.7<br>48.8; 6.0; 24.3<br>(183–186) |
| 154 | $CH_3$ | H | | HN⟨⟩S | $CH_3$ | −N⟨⟩S | H | H | 51.0; 5.6; 29.8<br>51.0; 5.5; 30.0<br>(83–85) |
| 155 | $CH_3$ | H | | HN⟨⟩SO | $CH_3$ | −N⟨⟩SO | H | H | 47.8; 5.2; 27.9<br>48.0; 5.3; 28.0<br>(150–153) |
| 156 | $CH_3$ | H | | HN⟨⟩$SO_2$ | $CH_3$ | −N⟨⟩$SO_3$ | H | H | 44.9; 4.9; 26.2<br>45.0; 4.9; 25.9<br>(183–185) |

EXAMPLE 157

Preparation of 7-Methyl-5-(1-piperazinyl)-1,2,4-triazolo[1,5-c]pyrimidine by Scheme IV A mixture of 6.00 g (33.3 mmole) of 7-methyl-5-methylthio-1,2,4-triazolo[4,3-c]pyrimidine, 30.0 g (0.35 mmole) of piperazine and 250 ml of dioxane was refluxed under nitrogen for six days. The mixture was cooled and concentrated in vacuo. The residue obtained was dissolved in 150 ml of water, and the solution was extracted four times with 150 ml portions of chloroform. The extracts were washed thrice with 150 ml portions of water and twice with 150 ml portions of sodium chloride solution and were dried over magnesium sulfate. Evaporation provided a yellow solid which was taken up in 150 ml of chloroform, filtered and chromatographed on a high pressure liquid chromatograph, eluting with methanol-ethyl acetate (1:1). Infrared and nuclear magnetic resonance spectral analyses showed fractions 2 and 3 to be 7-methyl-5-(1-piperazino)-1,2,4-triazolo-[1,5-c]pyrimidine, m.p. 92–95 C. Analysis: Calculated for $C_{10}H_{14}N_6$: %C, 55.0; %H, 6.5; %N, 38.5; Found: %C, 54.8; %H, 6.4; %N, 38.3. Fraction 4 contained about 15% of 7-methyl-5-(1-piperazino)-1,2,4-triazolo[4,3-c]pyrimidine.

EXAMPLE 158

Preparation of 7-Methyl-5-(4-methyl-1-piperazinyl)-1,2,4-triazolo[1,5-c]pyrimidine Using the method of Example 157, 7-methyl-5-methylthio-1,2,4-triazolo[4,3-c]pyrimidine was reacted with N-methylpiperazine to provide a mixture of 7-methyl-5-(4-methyl-1-piperazinyl)-1,2,4-triazolo[4,3-c]pyrimidine, m.p. 170°–171° C. and 7-methyl-5-(4-methyl-1-piperazinyl)-1,2,4-triazolo[1,5-c]pyrimidine, m.p. 95°–98° C. These compounds were separated by high pressure liquid chromatography using 5% methanol in ethyl acetate which contained a small amount of diethylamine.

EXAMPLE 159

Preparation of 7-Methyl-5-(4-morpholino)-1,2,4-triazolo[1,5-c]pyrimidine

A mixture of 6.0 g (33 mmole) of 7-methyl-5-methylthio-1,2,4-triazolo[4,3-c]pyrimidine and 15 ml of morpholine was heated at reflux for 19 hours, cooled and diluted with diethyl ether and hexane. The solid product was separated by filtration and chromatographed on florisil, eluting sequentially with benzene, 10% ethyl acetate in benzene, 50% ethyl acetate in benzene, and ethyl acetate. Early fractions were recrystallized from a benzene-hexane mixture to provide 7-methyl-5-(4-morpholino)-1,2,4-triazolo[1,5-c]pyrimidine, m.p. 113°–114° C. Later fractions were recrystallized from an ethyl acetate-hexane mixture with treatment with decolorizing charcoal to provide 7-methyl-5-(4-morpholino)-1,2,4-triazolo[4,3-c]pyrimidine, m.p. 209°–210° C.

EXAMPLE 160

To a solution of 3.00 g (10.8 mmole) of 2,5-diethyl-7-(4-thiomorpholino)-1,2,4-triaziolo[1,5-c]pyrimidine in 60 ml of warm ethanol was added 1.05 g (10.7 mmole) of concentrated sulfuric acid. The solution was diluted to 250 ml with diethyl ether and let stand for two hours. The precipitated product was separated by filtration and washed with ether and dried to provide 2,5-diethyl-7-(4-thiomorpholino)-1,2,4-triazolo[1,5-c]pyrimidine dihydrogen sulfate as a white solid, m.p. 178°–180° C. Analysis: Calculated for $C_{13}H_{19}H_5S.H_2SO_4$: %C, 41.5; %H, 5.6; %N, 18.7; Found: %C, 41.7; %H, 5.7; %N, 19.0.

EXAMPLE 161

To a solution of 1.75 g (6.31 mmole) of 2,5-diethyl-7-(4-thiomorpholino)-1,2,4-triazolo[1,5-c]pyrimidine in 20 ml of dioxane was added 1.0 ml of 6.4M hydrogen chloride (6.4 mmole) in ethanol. The solution was diluted with 100 ml of diethyl ether and allowed to stand several hours. The white solid was separated by filtration and dried to provide 2,5-diethyl-7-(4-thiomorpholino)-1,2,4-triazolo[1,5-c]pyrimidine hydrochloride hydrate, m.p. 113°–114° C. Analysis: Calculated for $C_{13}H_{19}N_5S.HCl.H_2O$: %C, 47.0; %H, 6.7; %N, 21.1; Found: %C, 46.9; %H, 6.8; %N, 21.3.

EXAMPLE 162

To a solution of 2.00 g (7.21 mmole) of 2,5-diethyl-7-(4-thiomorpholino)-1,2,4-triazolo[1,5-c]pyrimidine in 20 ml of warm ethanol was added 0.85 g (7.4 mmole) of phosphoric acid. The solution was diluted with 75 ml of diethyl ether and allowed to stand. After a few minutes the white solid was separated by filtration, washed with diethyl ether and dried to provide 2,5-diethyl-7-(4-thiomorpholino)-1,2,4-triazolo[1,5-c]pyrimidine trihydrogen phosphate hydrate, m.p. 154°–155° C. Analysis: Calculated for $C_{13}H_{19}N_5S.H_3PO_4.H_2O$: %C, 36.4; %H, 6.6; %N, 16.3; Found: %C, 36.5; %H, 5.8; %N, 16.6.

What is claimed is:

1. A compound of the formula

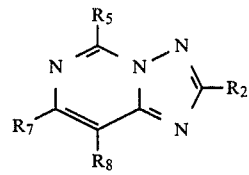

wherein $R_2$ is hydrogen or lower alkyl; at least one of $R_5$ and $R_7$ is

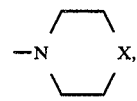

wherein each X is independently oxygen, sulfur, sulfinyl, sulfonyl, methylene, imido or lower N-alkylimido; one of $R_5$ and $R_7$ may also be hydrogen or lower alkyl; and $R_8$ is hydrogen, lower alkyl or phenyl; with the proviso that when $R_5$ only is a heterocyclic substituent, X is sulfinyl or sulfonyl; or a pharmaceutically acceptable salt thereof.

2. A compound of the formula

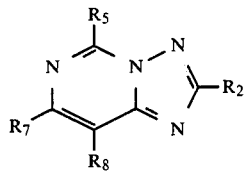

wherein R$_2$ is hydrogen or lower alkyl; R$_7$ is

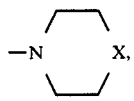

wherein X is oxygen, sulfur, sulfinyl, sulfonyl, methylene, imido or lower N-alkylimido; R$_5$ is hydrogen, lower alkyl or

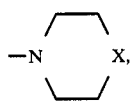

wherein X, independently of X in R$_7$, is oxygen, sulfur, sulfinyl, sulfonyl, methylene, imido or lower N-alkylimido; and R$_8$ is hydrogen, lower alkyl or phenyl; or a pharmaceutically acceptable salt thereof.

3. A compound according to claim 1, wherein X is sulfur or oxygen.

4. A compound according to claim 3, wherein R$_8$ is hydrogen.

5. A compound according to claim 2, wherein R$_5$ is hydrogen or lower alkyl.

6. A compound according to claim 2, wherein R$_8$ is hydrogen.

7. A compound according to claim 4, selected from the group consisting of
5,7-bis(4-morpholino)-1,2,4-triazolo[1,5-c]pyrimidine,
5-(1-morpholino)-7-(4-thiomorpholino)-1,2,4-triazolo[1,5-c]pyrimidine,
2-ethyl-5-methyl-7-(4-thiomorpholino)-1,2,4-triazolo[1,5-c]pyrimidine,
2-ethyl-5-methyl-7-(4-morpholino)-1,2,4-triazolo[1,5-c]pyrimidine,
2,5-diethyl-7-(4-thiomorpholino)-1,2,4-triazolo[1,5-c]pyrimidine,
2-ethyl-7-(4-morpholino)-5-n-propyl-1,2,4-triazolo[1,5-c]pyrimidine,
7-(4-morpholino)-5-n-propyl-1,2,4-triazolo[1,5-c]pyrimidine,
2-ethyl-5-n-propyl-7-(4-thiomorpholino)-1,2,4-triazolo[1,5-c]pyrimidine,
5-n-propyl-7-(4-thiomorpholino)-1,2,4-triazolo[1,5-c]pyrimidine,
5-ethyl-7-(4-morpholino)-1,2,4-triazolo[1,5-c]pyrimidine,
5-ethyl-2-methyl-7-(4-morpholino)-1,2,4-triazolo[1,5-c]pyrimidine, and
2,5-diethyl-7-(4-morpholino)-1,2,4-triazolo[1,5-c]pyrimidine.

8. The compound 2,5-diethyl-7-(4-thiomorpholino)-1,2,4-triazolo[1,5-c]pyrimidine or a pharmaceutically acceptable salt thereof according to claim 1.

9. The compound 2,5-diethyl-7-(4-morpholino)-1,2,4-triazolo[1,5-c]pyrimidine or a pharmaceutically acceptable salt thereof according to claim 1.

10. A pharmaceutical composition comprising an effective amount of a compound according to claim 1 and a pharmaceutically acceptable vehicle.

11. A bronchodilator pharmaceutical composition, comprising a compound according to claim 2 and a pharmaceutically accetable carrier, wherein said compound is present in an amount which is effective for obtaining bronchodilation.

12. A method for obtaining bronchodilation in a mammal, comprising administering an effective amount of a compound to said mammal, said compound being of the formula

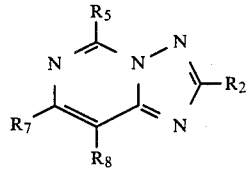

wherein R$_2$ is hydrogen or lower alkyl; at least one of R$_5$ and R$_7$ is

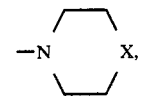

wherein each X is independently oxygen, sulfur, sulfinyl, sulfonyl, methylene, imido or lower N-alkylimido; one of R$_5$ and R$_7$ may also be hydrogen or lower alkyl; and R$_8$ is hydrogen, lower alkyl or phenyl; or a pharmaceutically acceptable salt thereof.

13. A method for obtaining bronchodilation in a mammal, comprising administering to said mammal a compound according to claim 2 in an amount which is effective for obtaining bronchodilation.

14. A method according to claim 12, wherein the compound is administered orally.

* * * * *